US005725473A

United States Patent [19]

Taylor

[11] Patent Number: 5,725,473

[45] Date of Patent: Mar. 10, 1998

[54] SEXUAL AID

[76] Inventor: Larry Thornell Taylor, 503 Woodland Hills Rd. West, Columbia, S.C. 29210

[21] Appl. No.: 520,135

[22] Filed: Aug. 28, 1995

[51] Int. Cl.$^6$ ........ A61F 5/00

[52] U.S. Cl. ........ 600/38; 601/46

[58] Field of Search ........ 600/38, 39, 41; 601/46, 69

[56] References Cited

U.S. PATENT DOCUMENTS

| | | | |
|---|---|---|---|
| 4,722,327 | 2/1988 | Harvey . | |
| 4,790,296 | 12/1988 | Segal . | |
| 4,834,075 | 5/1989 | Guo et al. . | |
| 5,067,480 | 11/1991 | Woog et al. | 601/46 |

*Primary Examiner*—Jennifer Bahr
*Assistant Examiner*—Rosiland Kearney
*Attorney, Agent, or Firm*—Richard C. Litman

[57] ABSTRACT

A sexual aid including a housing, mounted on detachable legs and containing a motor that urges a dildo, including vibration means, to describe an arcuate path generally coincident with an orifice, such as a vagina. A first stimulator, also containing vibration means, is superposed above the dildo and is urged through an arcuate path concentric with and radially spaced inwardly from that of the dildo, cyclically contacting a clitoris. The sexual aid may include means for introducing a vacuum between the first stimulator and the clitoris. A second stimulator, also containing vibration means, is subjacent the dildo and is urged through an arcuate path concentric with and radially spaced outwardly from that of the dildo, cyclically contacting an anus. The sexual aid includes remotely locatable stimulators that may be placed in contact with a user's nipples and areolae. The sexual aid also provides a vacuum phenomenon between the remotely locatable stimulators and the nipples.

7 Claims, 4 Drawing Sheets

SEXUAL AID

BACKGROUND OF THE INVENTION

1. Field of the Invention

This invention relates to sexual aids. More specifically, the present invention relates to powered devices that engage with a user and promote sexual stimulation.

2. Description of the Prior Art

Sexual drive is probably one of the most fundamental and urgent drives that humans experience. Unfortunately, as the large body of literature, counseling services and devices attest, this drive largely goes unsatisfied. Although psychology plays a large role in attaining satisfaction, physical excitation of the sex organs is a critical consideration.

The present invention is not intended to be limited for use with a particular sex organ. However, for brevity, discussion is directed toward use with the external female genitalia, or vulva.

The vulva surrounds the opening of the vagina, the musculomembranous tubular structure extending from the vulva to the uterine cervix. The vulva includes the clitoris, a highly sensitive sex organ which, when stimulated appropriately, provides sexual satisfaction. The clitoris, homologous to the penis, is a small cylindrical organ situated at the anterior part of the vulva.

During sexual intercourse, the penis is reciprocally and slidingly received in the vagina. The penis typically does not make substantial contact with the clitoris. Rather, the abdomen and the transition area from which the base of the penis extends provides the critical contact that may ultimately lead to sexual satisfaction. Sexual satisfaction in females generally is not derived from linear translation of the penis through the vagina, rather rhythmic pressure against and/or frictional engagement with the clitoris.

Women, for one reason or another, are not always successful in finding partners who satisfy their sexual drive. Some women, especially in view of such lethal sexually transmitted diseases such as acquired immunodeficiency syndrome, or AIDS, prefer to abstain rather than engage in human sexual relations. Although sexual relations may be avoided, whether ill-fated or non-disciplined, sexual drive may not. A need exists for an invention that provides for satisfaction of primal sexual drive yet eliminates reliance on human sexual interaction. Specifically, a need exists for a sexual aid that is adjustable to suit individual needs and provides intimate engagement with and appropriate stimulation of a clitoris.

Several types of sexual aids are described in the patent literature. Unfortunately, the apparatuses described provide singular excitation means which are received in a vagina in a linear path or engage with a vulva in an arcuately tangential path. For example, U.S. Pat. No. 4,722,327, issued Feb. 2, 1988, to William J. Harvey, describes a therapeutic apparatus. The apparatus includes a housing slidingly mounted on a base. The housing is reciprocally traversed along the base on rollers by a handle controlled by a user. A circular-shaped disk is eccentrically and rotatably mounted on the housing. A first end of an arm is rotatably and eccentrically mounted on the disk. A second end of the arm is rotatably mounted on the base. As the housing is traversed along the base relative to the second end of the arm, the first end compels the disk to rotate, defining a sinusoidal cam surface. A rod member having an outer and an inner end, slidingly mounted on the housing, has a roller mounted on the inner end that contacts the disk. A dildo member is mounted on the outer end of the rod member. The rod member is biased toward the disk. As the disk rotates, the dildo member is reciprocally and linearly traversed according to the cam surface. An annular pad is rearwardly disposed on the outer surface of the dildo member. In operation, the dildo member is reciprocally and slidingly received in the vagina. The dildo member translates linearly such that the annular pad systematically contacts the vulva.

U.S. Pat. No. 4,790,296, issued Dec. 13, 1988, to Daniel A. Segal, describes a sexual stimulation apparatus. The apparatus includes a housing with a motor mounted therein. A disk member is rotatably mounted on the housing. The motor rotates the disk member. A rod member having an inner and an outer end is slidingly received in the housing. A dildo member is mounted on the outer end of the rod member. An arm has a first end eccentrically and rotatably mounted on the disk member. The arm has a second end rotatably mounted on the inner end of the rod member. As the disk member is rotated, the arm urges the dildo member to reciprocally and linearly translate. In operation, the dildo member is linearly and reciprocally received in a vagina. No means for contacting the vulva is described.

U.S. Pat. No. 4,834,075, issued May 30, 1989, to Yuh-Kuen Guo et al., describes an electromechanical message apparatus. The device includes a housing with a motor mounted therein. A disk member is rotatably mounted on the housing. The motor rotates the disk member. A rod member has an inner end rotatably mounted on the housing. A massaging member is mounted on the outer end of the rod member. An arm has a first end eccentrically and rotatably mounted on the disk member. The arm has a second end rotatably mounted on the first end of a slide member. The slide member is received in a sleeve and has a second end rotatably mounted at a mid-point on the rod member. As the disk member is rotated, the arm urges the slide member to translate linearly, transversely against the rod member. The massaging member reciprocally defines an arcuate path tangential to a vulva. In operation, the massaging member may be directed to systematically brush a body surface, presumably the clitoris.

Clearly, the above demonstrates a need for a sexual aid providing multiple excitation means that contact the clitoris in a locally arcuate path radially spaced inwardly from the path coincident with a vagina.

None of the above references, taken alone or in combination, are seen as teaching or suggesting the presently claimed sexual aid.

SUMMARY OF THE INVENTION

The present invention overcomes the limitations of the above inventions by providing a sexual aid with multiple excitation means that contact the vagina, clitoris and anus in locally arcuate paths coincident with the vagina. The invention includes a housing detachably mounted on two legs. One embodiment provides for a motor mounted on the housing. The motor includes an output shaft that rotates a lever. The lever is pivotally mounted on an a connecting rod. The connecting rod also is pivotally mounted on an arm. The arm has a first end rotatably mounted on the housing and a second end that extends toward an aperture in the housing in a pendulum-like manner. In operation, the motor output shaft rotates the lever, urging the connecting rod to swing the arm relative to the aperture of the housing. An alternative embodiment provides for the motor to be mounted on, for pivoting with, the arm and the connecting rod being rotatably mounted on the housing.

An adaptor plate is mounted on the second end of the arm. A dildo is mounted on the adaptor plate. The dildo may include vibrator means therein. A first stimulator is mounted on the adaptor plate, superposed above the dildo for contacting the clitoris. The first stimulator may include vacuum means and/or vibrator means therein. The first stimulator, having a suction cup-like embodiment, may be detached from the housing and coupled with two suction cup-like second stimulators. The combination of suction cup-like stimulators are all in fluid communication with a flexible conduit having a distal end. A squeeze ball may be received in the distal end to introduce a vacuum therein. The user may suck on the distal end to induce the vacuum phenomenon. A third stimulator is mounted on the adaptor plate, subjacent the dildo member. The third stimulator also may include vibrator means therein.

In operation, the arm urges the adaptor plate through an arcuate path. The dildo is slidingly received in a vagina, the first stimulator periodically rubs against the clitoris and the third stimulator is slidingly received in an anus. The second stimulators periodically induce a vacuum condition over the user's nipples.

In consideration of the above, an object of the invention is to provide a sexual aid that satisfies sexual drive.

Another object of the invention is to provide a sexual aid having multiple excitation means that cyclically contact the vagina.

A further object of the invention is to provide a sexual aid having multiple excitation means that cyclically contact the clitoris.

An additional object of the invention is to provide a sexual aid that cyclically contacts the anus.

Yet another object of the invention is to provide a sexual aid that induces a vacuum phenomenon over a user's nipples.

Yet a further object of the invention is to provide a sexual aid that is readily mobile.

Yet an additional object of the invention is to provide a sexual aid including means to oscillate stimulation means through an arcuate path.

Still another object of the invention is to provide improved elements and arrangements thereof in an apparatus for the purposes described which is inexpensive, dependable and fully effective in accomplishing its intended purposes.

These and other objects of the present invention will become readily apparent upon further review of the following specification and drawings.

DETAILED DESCRIPTION OF THE PREFERRED EMBODIMENTS

Figure 1:
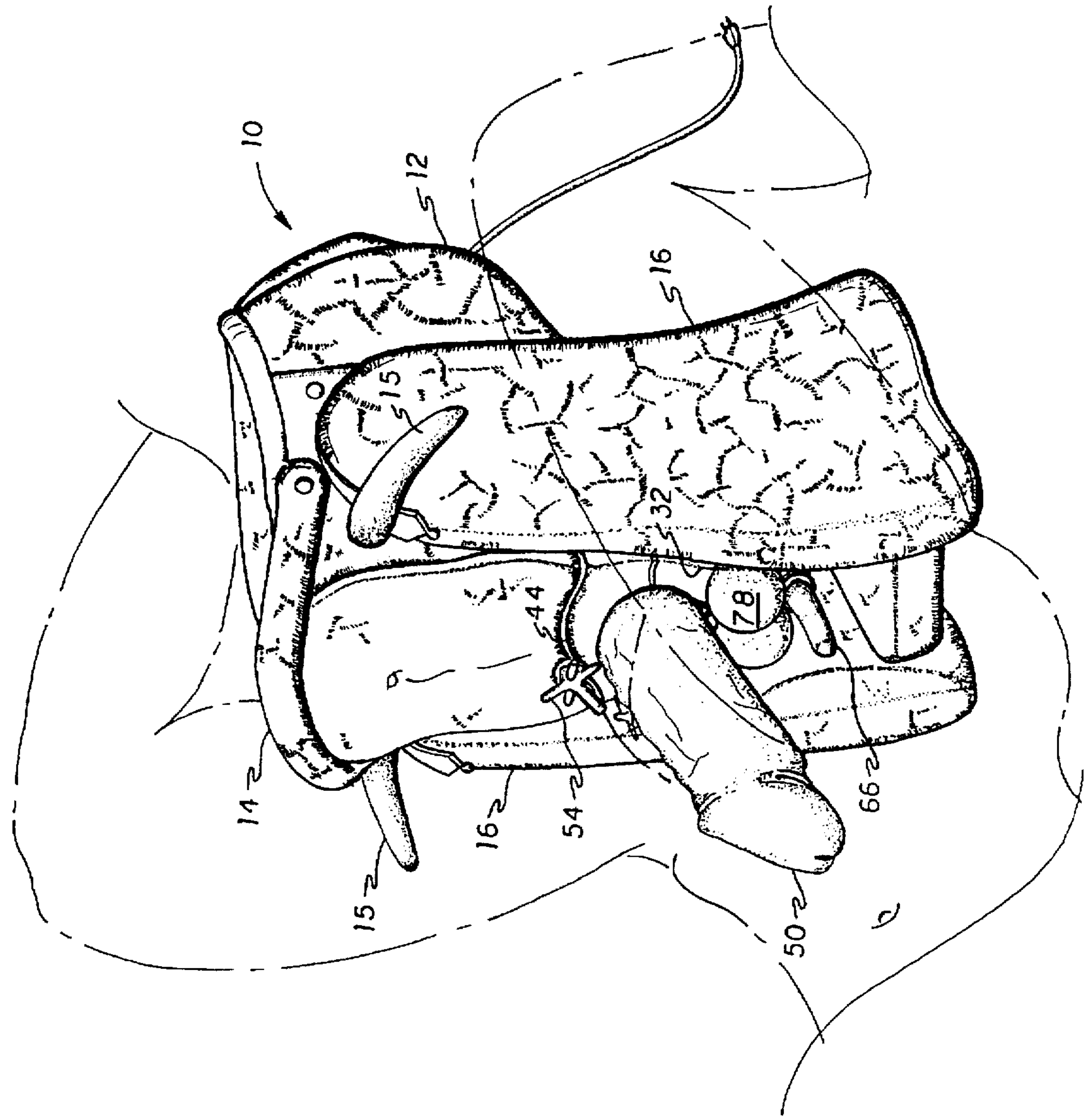
FIG. 1 is an environmental perspective view of the invention engaging with a user's vagina, clitoris and anus, the user's body shown in ghost lines.
Figure 2:
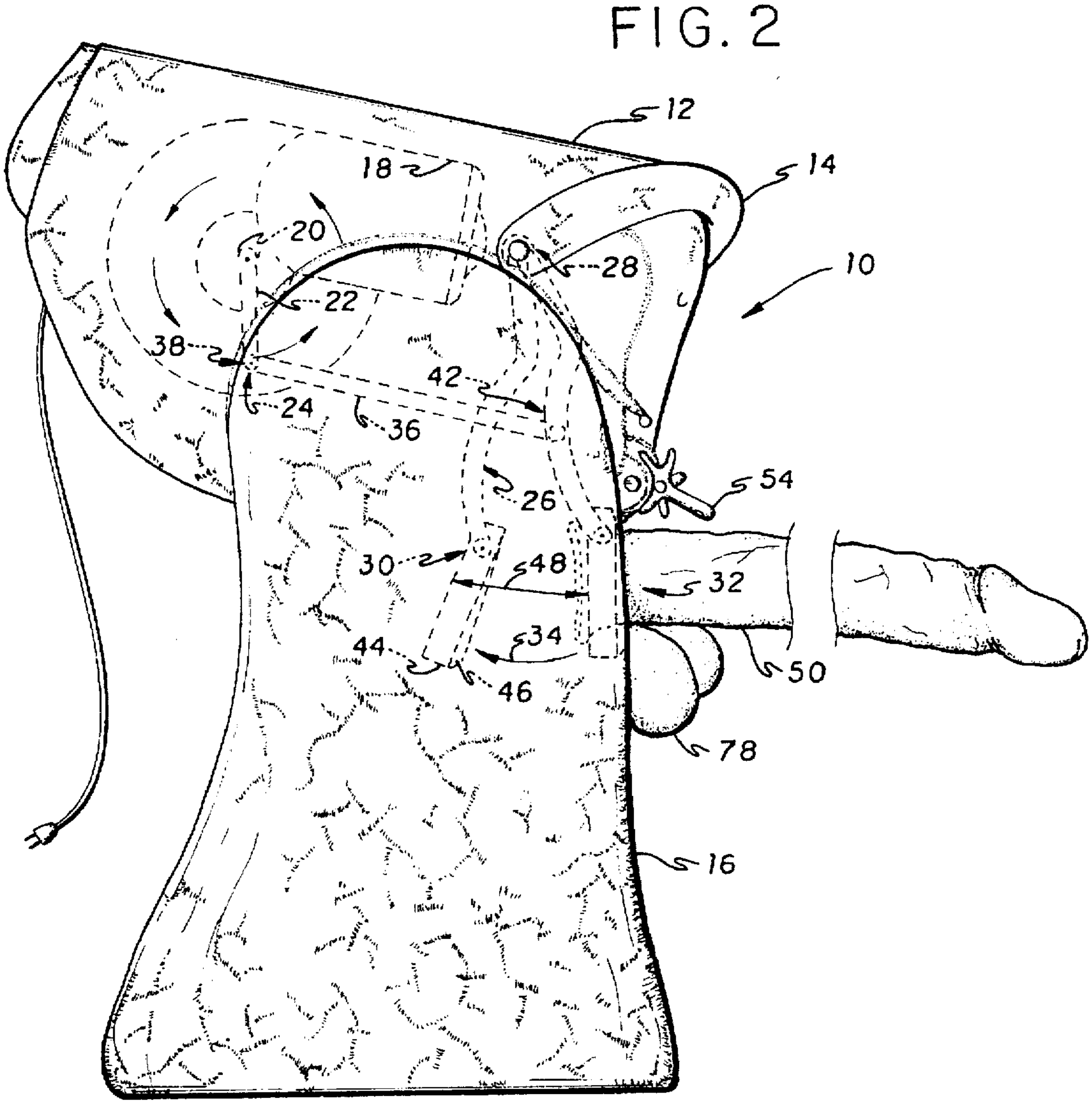
FIG. 2 is a side elevational view of the invention with the motor and moving elements shown in ghost lines.

Referring to FIGS. 1 and 2, the invention 10 is shown including a housing 12. Preferably, the housing 12 is approximately 11.5 inches long, 7 inches wide and 6 inches deep. The housing 12 includes a first handle 14 for convenient transportation thereof. Preferably, the first handle 14 is situated in the front of the housing 12, providing the user with convenient means for optimal positioning of the invention 10. Additionally, the housing 12 may include two second handles 15. The second handles 15 provide the user with means for maintaining the user's position relative to the invention 10 and/or adjusting the attitude of the invention 10 to suit the users purposes.

The housing 12 is detachably mounted on two legs 16. Preferably, the legs 16 are approximately 8.5 inches tall. When mounted on the legs 16, the housing 12 is situated approximately 15 inches above the surface on which the invention 10 is disposed. The housing 12 is rotatably adjustable relative to the legs 16, enabling the user to customize the attitude of the invention 10 to suit the user's purposes. The detachability of the housing 12 and legs 16 renders the invention 10 more easily transportable.

As best shown in FIG. 2, the invention 10 includes an electric motor 18 mounted within the housing 12. The motor 18 may be, but is not be limited to being selected from the group including: fluid-powered motors, gasoline-powered motors, diesel-powered motors, solar energy-powered motors and the like. The motor 18 has an output shaft 20 with a lever 22 that extends toward a distal end 24. The motor 18 rotates the lever 22, defining a vertical, disk-shaped path. The disk-shaped path may assume a vertical, horizontal or intermediate attitude, so long as the distal end 24 of the lever 22 traverses fore and aft relative to the housing 12 during rotation.

The invention 10 also includes an arm 26 having a first end 28 rotatably mounted on the housing 12. The arm 26 has a second end 30 that extends downwardly toward an aperture 32 in the housing 12, as best shown on FIG. 1. The arm 26 pivots about the first end 28 similar to a pendulum. Turning back to FIG. 2, superposing the pivot point of the arm 26, i.e. the first end 28, above the aperture 32 contributes to the preferred, upwardly arcing path 34 the arm 26 defines, discussed infra. However, the arcuate path 34 may be adjusted to curve downwardly or laterally, respecting the user's particular needs.

The invention 10 further includes a connecting rod 36 having a first end 38 rotatably mounted on the distal end 24 of the lever 22. The connecting rod 36 has a second end 42 rotatably mounted on a mid-point on the arm 26. As the lever 22 rotates, it urges the connecting rod 36 to translate fore and aft, urging the arm 26 to cyclically pivot about the pivot point, or first end 28, of the arm 26, defining the preferred arcuate path 34.

Figure 3:
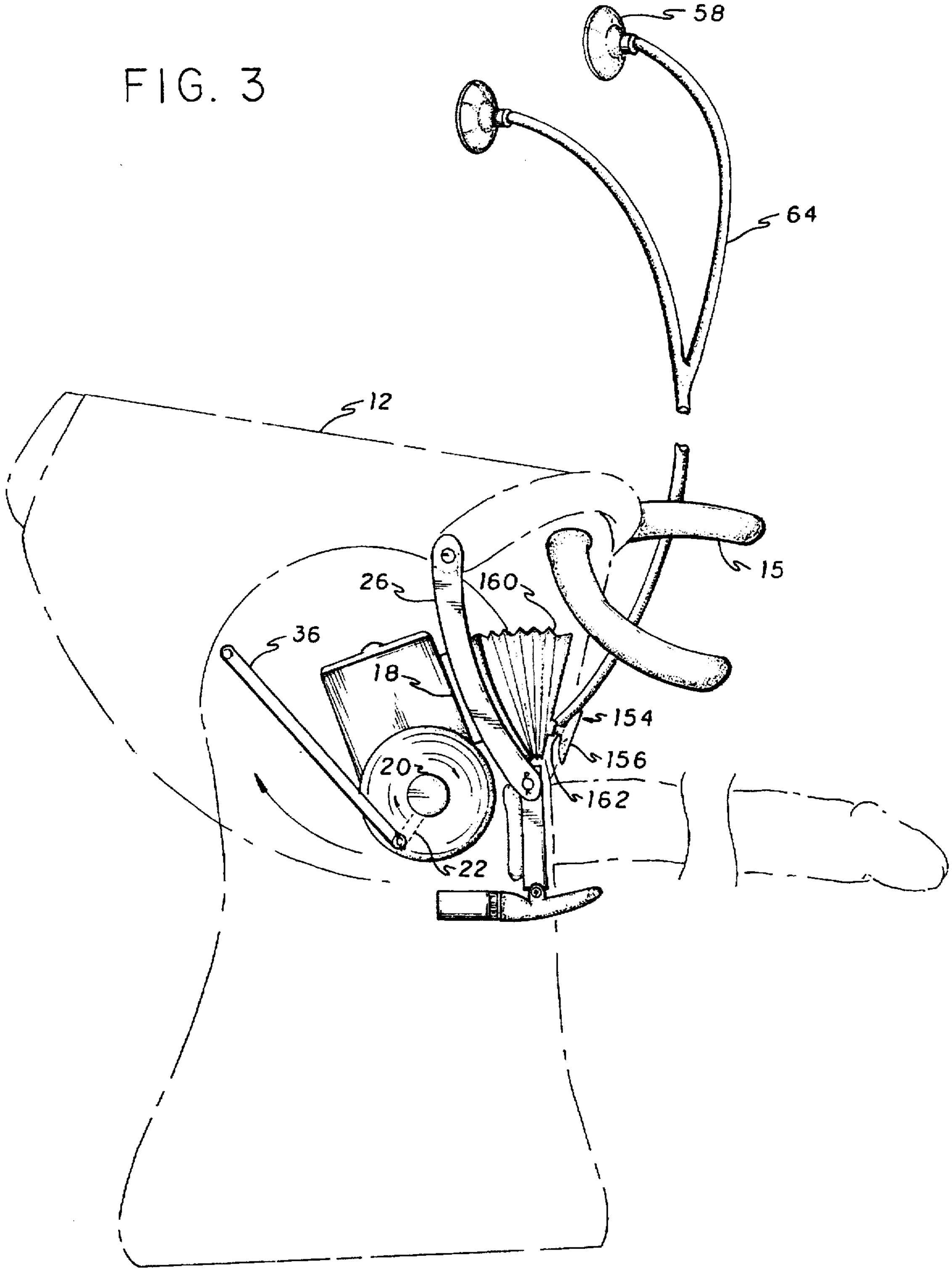
FIG. 3 is a side elevational view of another embodiment of the invention with the housing and legs shown in ghost lines.

Referring to FIG. 3, an alternative embodiment of the drive mechanism is shown with the motor 18 mounted on the arm 26. As in the original embodiment, the lever 22 mounted on the output shaft 20 of the motor 18 is pivotally mounted on the connecting rod 36. The connecting rod 36 is pivotally mounted on the housing 12. As the output shaft 20 rotates, the lever 22 urges the connecting rod 36 against the housing 12, oscillating the arm 26 along with the motor 18.

Referring also to FIGS. 1 and 2, the invention additionally includes an adaptor plate 44, having a front surface 46, situated in the aperture 32 of the housing 12. The adaptor plate 44 is adjustably, but rigidly mounted on the arm 26. Oscillation of the arm 26 imparts reciprocating arcuate motion of the adaptor plate 44 between the aperture 32 and a predetermined arcuate distance 48 within the housing 12. Preferably, the arcuate distance 48 is approximately 4.5 inches; however, the arcuate distance 48 may be adjusted to suit the user's purposes.

A dildo 50 having a predetermined length is mounted on the front surface 46 of the adaptor plate 44. The dildo 50 may assume any shape or texture, respecting the user's preferences. The dildo 50 may include vibrating means (not shown) for imparting vibration therein. Preferably, the dildo 50 is slidingly received in the user's vagina 52.

Referring only to FIGS. 1 and 2, a first stimulator 54 also is mounted on the adaptor plate 44. The first stimulator 54 may assume any shape or texture, respecting the user's preferences. The first stimulator 54 also may include vibrating means (not shown) for imparting vibration therein. The first stimulator 54, preferably, contacts the user's clitoris 56.

The first stimulator 54 is shown mounted on the adaptor plate 44 above the dildo 50. The first stimulator 54 defines an arcuate path concentric with and radially spaced within the arcuate path defined by the dildo 50 when the invention 10 is placed in service. This orientation is preferred when the user is situated such that the vagina is subjacent to the clitoris, thereby providing simultaneous engagement with and excitation of the vagina and clitoris. However, the arrangement may be configured in any manner suited to the user's purposes. Notwithstanding orientation, the radial spacing of the first stimulator 54 relative to the dildo 50 may be adjusted, respecting the user's body configuration.

Referring only to FIG. 3, a second embodiment of the first stimulator 154 is shown. The first stimulator 154 includes a suction cup member 156 that conformingly and sealingly receives the upper portion of the vulva. The suction cup member 156 of the first stimulator 154 is more specifically directed at receiving the clitoris. The suction cup member 156 is in fluid communication with a bellows 160 or squeeze ball (not shown) via flexible conduit 162. As the arm 26 oscillates relative to the housing, the arm 26 compresses and expands the bellows 160 relative to the housing 12. The arm 26 and bellows 160 cyclically introduce a vacuum in the volume defined by the suction cup member 156 and the portion of the vulva received therein. The cyclical vacuum phenomenon stimulates the clitoris.

Figure 4:
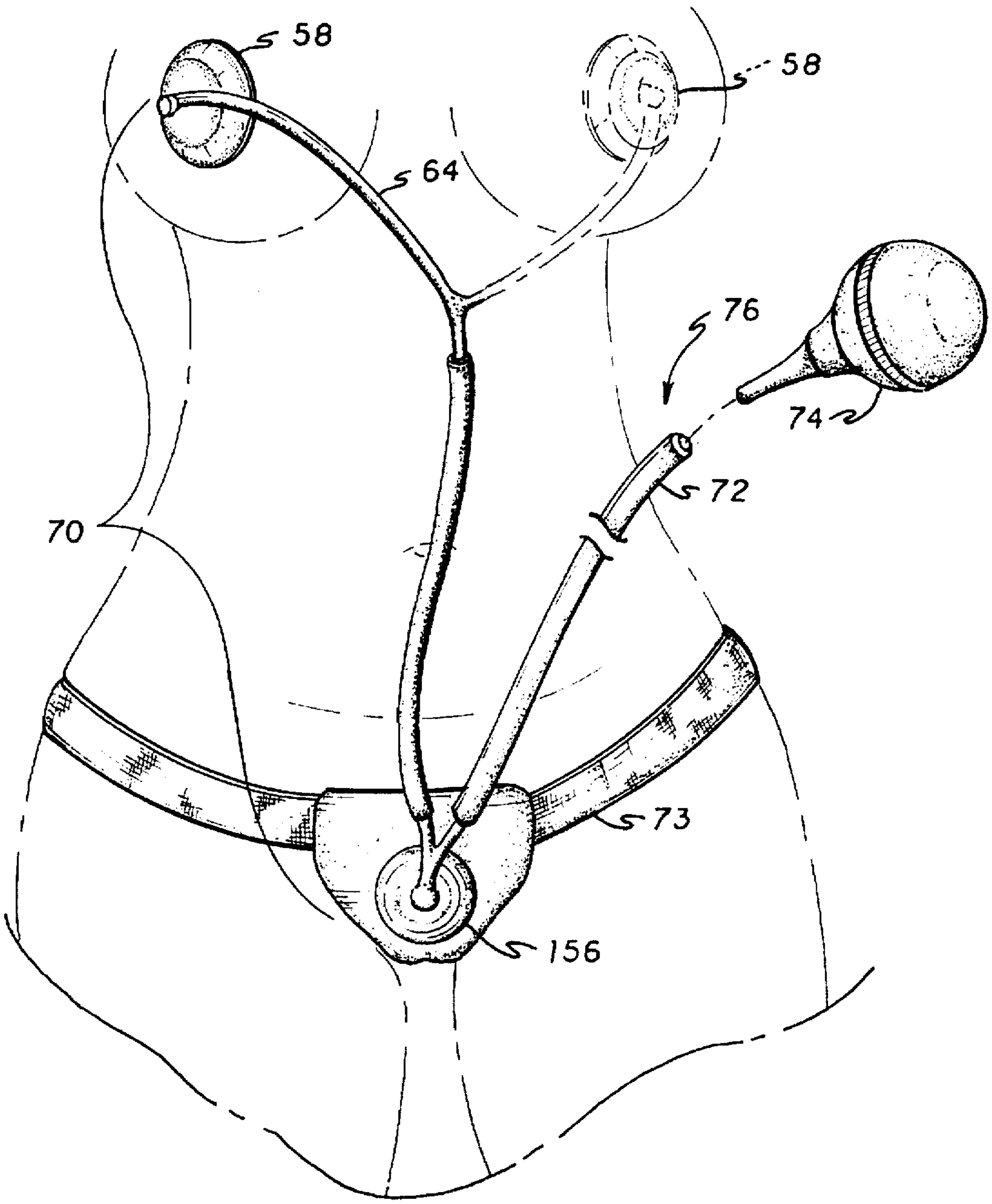
FIG. 4 is a front elevational view of yet another embodiment of the invention, the female body parts shown in ghost lines. Similar reference characters denote corresponding features of the invention consistently throughout the attached drawings.

The invention 10 also provides additional suction cup members 58 conformingly and sealingly receive the user's nipples and areolae, as shown on FIG. 4. The additional suction cup members 58 also are in fluid communication with the bellows 160 via flexible conduit 64. The bellows 160 cyclically introduces a vacuum phenomenon in the volume defined by each additional suction cup member 58 to stimulate the user's nipples.

Referring to FIG. 4, the invention 10 provides for a portable and secretable embodiment including the suction cup member 156 of the first stimulator 154 and the two additional suction cup members 58. The first suction cup member 156 and second suction cup members 58 may be detached from the housing 12. The assembly 70 includes additional flexible conduit 72 in communication with the suction cup member 156 and also with the additional suction cup members 58 via the flexible conduit 64. The assembly 70 may be secured to the user's body with an adjustable girdle 73. A squeeze ball 74 is shown being received in the distal end 76 of the flexible conduit 72 permitting user-controlled introduction of vacuum in the volumes defined by the first suction cup member 156 and additional suction cup members 58, and the body parts placed in association therewith, as described above. An alternative embodiment provides for the user introducing the vacuum phenomenon be sucking on the distal end 76 of the flexible conduit 72 with the user's mouth (not shown). Either embodiment provides for a portable, sexually stimulating device that may be concealed beneath the user's clothing.

Referring again to FIG. 1, a second stimulator 66 is mounted on the adaptor plate 44. The second stimulator 66 may assume any shape or texture, respecting the user's preferences. The second stimulator 66 also may include vibrating means (not shown) for imparting vibration therein. The second stimulator 66, preferably, contacts the user's anus.

The second stimulator 66 is shown mounted on the adaptor plate 44 below the dildo 50. The second stimulator 66 defines an arcuate path concentric with and radially spaced within the arcuate path defined by the dildo 50 when the invention 10 is placed in service. This orientation is preferred when the user is situated such that the user's anus is subjacent to the vagina, thereby providing simultaneous engagement with and excitation of the vagina and anus. However, the arrangement may be configured in any manner suited to the user's purposes. Notwithstanding orientation, the radial spacing of the second stimulator 66 relative to the dildo 50 may be adjusted, respecting the user's body configuration.

Referring also to FIG. 2, the invention 10 also provides pseudo-testicles 78 loosely mounted proximate to and depending from the adaptor plate 44 or the dildo 50. The pseudo-testicles 78 are intended to contact the user when the apparatus is being used, thus simulating the tactual sensation created by real testicles.

In operation, the dildo 50 is slidingly received in a vagina lengthwise. Unlike the prior art, the dildo 50 defines an arcuate path generally coincident with the user's vagina. The first stimulator 54 contacts the clitoris at the end of each arcuate stroke of the arm 26. The cyclical contact of the first stimulator 54 with the clitoris contributes to sexual satisfaction.

Prior inventions provide for linear translation coincident with the vagina or arcuate brushing tangent to the vulva. The coincident arcuate path provided by the instant invention 10 represents a significant advance over the prior art because it more closely approximates the motion assumed by a man urging his penis to translate within the vagina during sexual intercourse. Rhythmic pressure against the walls of the vagina, rather than linear translation thereacross, is known to have a more stimulating effect. Additionally, inward frictional engagement with the clitoris, rather than brushing thereacross, is known to have a more stimulating effect. The present invention 10 advances significantly over the prior art by providing both. The preferred embodiment of the invention 10 combines the two stimulus means, conferring on its users real-world satisfaction of sexual drive without real-world anxieties.

The present invention 10 is not intended to be limited to the embodiments described above, but to encompass any and all embodiments within the scope of the following claims.

I claim:

1. A sexual aid apparatus comprising:
   - a housing;
   - a dildo having a length;
   - a pair of pseudo-testicles loosely mounted proximate to said dildo: and
   - drive means for urging said dildo through an arcuate path generally coincident with said length of said dildo relative to said housing.

2. A sexual aid apparatus as recited in claim 1, including at least one leg adjustably mounted on said housing, said at least one leg elevating said housing above a surface.

3. A sexual aid apparatus as recited in claim 1, said dildo including vibration means for generating vibrations in said dildo.

4. A sexual aid apparatus as recited in claim 1, said drive means including:

a motor including an output shaft mounted on said housing;

a lever extending from said output shaft and having a distal end;

an arm having a first end rotatably mounted on said housing and a second end drivingly connected to said dildo; and a connecting rod interposed between said distal end of said lever and a mid-point on said arm;

whereby said motor rotates said lever within a plane, urging said connecting rod to oscillate said arm.

5. A sexual aid apparatus comprising:

a housing;

a dildo having a length;

drive means for urging said dildo through an arcuate path generally coincident with said length of said dildo relative to said housing; and at least one stimulator mounted relative to said dildo at a predetermined distance therefrom, said at least one stimulator including vibration means for generating vibrations in said at least one stimulator.

6. A sexual aid apparatus as recited in claim 5, said at least one stimulator being superposed above said dildo.

7. A sexual aid apparatus as recited in claim 5, said at least one stimulator being subjacent said dildo.

* * * * *